United States Patent
Smith (10) Patent No.: US 8,186,363 B2
(45) Date of Patent: May 29, 2012

(54) APPLICATOR FOR IMPROVED APPLICATION OF A HAIR TREATMENT COMPOSITION TO A BUNDLE OF HAIR STRANDS

(75) Inventor: Paul James Smith, Twickenham (GB)

(73) Assignee: The Procter & Gamble Company, Cincinnati, OH (US)

( * ) Notice: Subject to any disclaimer, the term of this patent is extended or adjusted under 35 U.S.C. 154(b) by 103 days.

(21) Appl. No.: 12/622,762

(22) Filed: Nov. 20, 2009

(65) Prior Publication Data

US 2010/0139685 A1 Jun. 10, 2010

(30) Foreign Application Priority Data

Dec. 10, 2008 (EP) .................................... 08021438

(51) Int. Cl.
*A45D 19/18* (2006.01)
*A61K 8/18* (2006.01)
*A61Q 5/08* (2006.01)
*A61Q 5/10* (2006.01)
*B65D 43/14* (2006.01)
*B65D 51/04* (2006.01)
*A46B 11/00* (2006.01)

(52) U.S. Cl. ........... 132/270; 132/208; 220/848; 401/10

(58) Field of Classification Search .................. 132/270, 132/200, 202, 207, 208, 212, 272, 273, 274, 132/234, 244, 221, 222, 108–112; 401/9, 401/10, 207, 196, 203, 261; 220/848; 8/405, 8/406, 408, 435, 151; 68/200, 205 R
See application file for complete search history.

(56) References Cited

U.S. PATENT DOCUMENTS

| | | | |
|---|---|---|---|
| 2,272,409 A | | 2/1942 | Johnson |
| 2,310,295 A | | 2/1943 | Keele |
| 2,761,459 A | * | 9/1956 | Kaul ............................. 132/109 |
| 2,776,667 A | | 1/1957 | Fitzgerald |
| 3,030,968 A | | 2/1960 | Oberstar |
| 2,962,031 A | | 11/1960 | Bumgarner |
| 3,128,778 A | * | 4/1964 | Ricci et al. .................... 132/212 |
| 3,662,767 A | | 5/1972 | Murtha |
| 3,702,508 A | | 11/1972 | Netter |
| 3,921,647 A | | 11/1975 | Fisher |
| 4,020,854 A | | 5/1977 | Caruso |
| 4,108,184 A | | 8/1978 | Morganroth |
| 4,398,549 A | | 8/1983 | Thomas |

(Continued)

FOREIGN PATENT DOCUMENTS

DE 662702 C1 7/1938

(Continued)

*Primary Examiner* — Todd Manahan
*Assistant Examiner* — Vanitha Elgart
(74) *Attorney, Agent, or Firm* — Carl J. Roof (57) ABSTRACT

The present invention relates to an applicator (1) which allows for precise, non-messy and even application of a hair treatment composition to a hair strand. The applicator (1) comprises a plate (10) movably joined by a connection (30) to a well (20), a first fin (70) and a second fin (71) which project from the internal surface (101) of the plate (10) and point to one another and a fluid metering element comprising a lower metering portion (50) positioned on the internal surface of the wall (202) of the well (20) adjacent the rim (222). When said applicator (1) is in a closed state, the lower metering portion (50) and the first fin (70) are substantially juxtaposed to provide said fluid metering element.

13 Claims, 2 Drawing Sheets

U.S. PATENT DOCUMENTS

| | | | |
|---|---|---|---|
| 4,503,870 A | 3/1985 | Peterson | |
| 4,671,302 A * | 6/1987 | Hill | 132/212 |
| 4,727,893 A * | 3/1988 | Goncalves | 132/320 |
| 4,796,812 A | 1/1989 | Grollier | |
| 4,942,893 A | 7/1990 | Trottier | |
| 5,042,514 A | 8/1991 | Bastien | |
| 5,060,679 A | 10/1991 | Christopher | |
| 5,228,465 A * | 7/1993 | Hill | 132/212 |
| 5,279,313 A | 1/1994 | Clausen | |
| 5,535,764 A | 7/1996 | Abramson | |
| 5,554,197 A | 9/1996 | Assini | |
| 5,706,839 A * | 1/1998 | Patti | 132/277 |
| 5,771,906 A | 6/1998 | De Benedictis | |
| 5,823,204 A | 10/1998 | Todd | |
| 5,848,730 A | 12/1998 | Kawase | |
| 5,971,645 A | 10/1999 | Fukushima | |
| 6,062,231 A | 5/2000 | De Laforcade | |
| 6,148,829 A | 11/2000 | De Benedictis | |
| 6,250,312 B1 | 6/2001 | Dasilva | |
| 6,427,701 B1 | 8/2002 | Roth | |
| 6,440,175 B1 | 8/2002 | Stanley | |
| 6,626,599 B2 | 9/2003 | Delaforcade | |
| 6,746,165 B2 * | 6/2004 | de Laforcade | 401/10 |
| 6,748,957 B1 | 6/2004 | Giordano | |
| 7,025,069 B2 | 4/2006 | Thiebaut | |
| 7,156,885 B2 * | 1/2007 | Kennedy et al. | 8/405 |
| 7,198,049 B2 | 4/2007 | Elmer | |
| 7,357,137 B2 | 4/2008 | Husband | |
| 7,425,220 B2 | 9/2008 | Barrass | |
| 7,475,688 B2 | 1/2009 | Colacioppo | |
| 7,543,591 B1 | 6/2009 | Munsil | |
| 2002/0114657 A1 | 8/2002 | Gueret | |
| 2002/0142027 A1 | 10/2002 | Gueret | |
| 2003/0007825 A1 | 1/2003 | De Laforcade | |
| 2004/0016064 A1 | 1/2004 | Vena | |
| 2004/0031502 A1 | 2/2004 | Winckels | |
| 2004/0089316 A1 | 5/2004 | Hamilton | |
| 2004/0182408 A1 | 9/2004 | De LaForcade | |
| 2005/0079192 A1 | 4/2005 | Simon | |
| 2005/0207153 A1 | 9/2005 | Leleve | |
| 2005/0211599 A1 | 9/2005 | De LaMettrie | |
| 2006/0042643 A1 | 3/2006 | Delan | |
| 2006/0064824 A1 | 3/2006 | Godfrey | |
| 2006/0090771 A1 | 5/2006 | Ramet | |
| 2006/0144415 A1 | 7/2006 | Magee | |
| 2006/0207036 A1 | 9/2006 | Kennedy | |
| 2007/0144550 A1 | 6/2007 | Roher | |
| 2007/0215170 A1 | 9/2007 | Kennedy | |
| 2007/0227620 A1 | 10/2007 | Kunii | |
| 2008/0000492 A1 | 1/2008 | Mills | |
| 2008/0083418 A1 | 4/2008 | Glenn | |
| 2008/0083419 A1 | 4/2008 | Glenn | |
| 2008/0083420 A1 | 4/2008 | Glenn | |
| 2008/0087292 A1 | 4/2008 | Abergel | |
| 2008/0087293 A1 | 4/2008 | Glenn | |
| 2008/0087294 A1 | 4/2008 | Glenn | |
| 2008/0110929 A1 | 5/2008 | Stanley | |
| 2008/0156817 A1 | 7/2008 | Roseblade | |
| 2008/0196734 A1 | 8/2008 | Husband | |
| 2008/0223386 A1 | 9/2008 | Albisetti | |
| 2008/0223391 A1 | 9/2008 | Baker | |
| 2008/0223393 A1 | 9/2008 | Boyle | |
| 2008/0257370 A1 | 10/2008 | Perry | |
| 2008/0308119 A1 | 12/2008 | Smith | |
| 2009/0050171 A1 | 2/2009 | Barrass | |
| 2009/0071496 A1 | 3/2009 | Glenn | |
| 2009/0084393 A1 | 4/2009 | Baker | |
| 2009/0084394 A1 | 4/2009 | Baker | |
| 2009/0084395 A1 | 4/2009 | Glenn | |
| 2009/0095314 A1 | 4/2009 | Lund | |
| 2009/0101159 A1 | 4/2009 | Bonnafous | |
| 2009/0152281 A1 | 6/2009 | Bowes | |
| 2009/0223531 A1 | 9/2009 | Lund | |
| 2010/0139683 A1 * | 6/2010 | Smith | 132/208 |
| 2010/0139684 A1 * | 6/2010 | Smith et al. | 132/208 |
| 2010/0175704 A1 * | 7/2010 | Gueret | 132/200 |

FOREIGN PATENT DOCUMENTS

| | | |
|---|---|---|
| DE | 197639177 U1 | 4/1977 |
| DE | 198805283 U1 | 7/1988 |
| DE | 3138389 C2 | 7/1990 |
| DE | 4041742 A1 | 6/1992 |
| DE | 29616331 U1 | 12/1996 |
| DE | 29917054 U1 | 8/2000 |
| DE | 10259016 A1 | 6/2004 |
| DE | 202004017014 U1 | 6/2005 |
| DE | 20221665 U1 | 11/2006 |
| DE | 102005058188 A1 | 6/2007 |
| DE | 202007016018 U1 | 4/2008 |
| EP | 1138374 A1 | 10/2001 |
| EP | 1566114 A1 | 8/2005 |
| EP | 1264559 B1 | 11/2005 |
| EP | 1897459 A1 | 3/2008 |
| EP | 1915920 A1 | 4/2008 |
| EP | 1481605 B1 | 8/2009 |
| FR | 2444421 A1 | 7/1980 |
| FR | 2495905 A1 | 6/1982 |
| FR | 2854778 A1 | 11/2004 |
| FR | 2905833 A1 | 3/2008 |
| GB | 274875 A | 10/1927 |
| GB | 2242357 A | 10/1991 |
| GB | 2383944 A | 7/2003 |
| GB | 2384425 A | 7/2003 |
| JP | 4-41305 | 4/1992 |
| JP | 11-178630 | 7/1999 |
| JP | 11-178639 A | 7/1999 |
| JP | 2001-211925 A | 8/2001 |
| JP | 2002-034636 A | 2/2002 |
| JP | 2003-199623 A | 7/2003 |
| JP | 2003-310337 A | 11/2003 |
| WO | WO 93/02589 A1 | 2/1993 |
| WO | WO 93/10687 A1 | 6/1993 |
| WO | WO 98/43511 A1 | 10/1998 |
| WO | WO 02/074129 A1 | 9/2002 |
| WO | WO 2006/010354 A1 | 2/2006 |

* cited by examiner

Fig.1.

APPLICATOR FOR IMPROVED APPLICATION OF A HAIR TREATMENT COMPOSITION TO A BUNDLE OF HAIR STRANDS

FIELD OF THE INVENTION

The present invention relates to an applicator which allows for precise, non-messy and even application of a cosmetic composition to fibres, preferably keratinous fibres. The applicator, which comprises a first and a second fin and a fluid metering means, is especially intended for a hair treatment composition to provide hair strand effects.

BACKGROUND OF THE INVENTION

Application of hair treatment compositions to distinct hair strands allows the user to achieve a different look than a full head application. Hair treatment compositions for providing a hair strand effects include highlighting compositions, dyeing compositions, perming compositions, styling compositions and mixtures thereof.

Hair strand effects such as those provided by highlighting compositions and dyeing compositions must be precisely applied where desired. For example, if a too abundant amount of highlighting composition is applied to the root, it may transfer to the neighbouring unselected hair strands. This may alter the overall end result and may totally disrupt the pattern that the user has tried to create. If an excessive amount of product is applied to the root, the colour effect will not be consistent along the length of the hair, leading to an undesired visual effect. If, instead, insufficient composition is applied to the hair strands, the evenness of the hair strand effect may not be achieved producing an end result which is visually unacceptable. Hence it is important that a consistent amount of product is applied uniformly along the hair strands being treated.

One known method for providing hair strand effects such as highlighting is the cap and hook system. A cap, provided with holes, is positioned over the head and hair strands are pulled out with a hook. Far from being accurate, the cap and hook system suffers from several drawbacks including random selection of the hair strands via the holes on the cap and the likelihood of applying the highlighting composition to only a portion of the selected hair strands and not to the root portion.

Several applicators have been designed for application of a hair treatment composition to independent bundles of hair strands as alternatives to the cap and hook system. These applicators belong to two general fields. One field comprises applicators based on combs and/or brushes. The other group comprises applicators having two articulated portions which are movable one relative to the other. Many attempts have been disclosed in this later field. U.S. Pat. No. 3,030,968 refers to an applicator for liquid treating material to be loaded by immersion. This applicator comprises a trough and a hair guide member mounted on the ends of the legs of a U-shaped resilient spring. The spring allows for manual compression and permits the hair guide member to fit into the trough. U.S. Pat. No. 6,062,231 discloses a device for applying a hair product to hair strands. This device comprises two articulated portions; the application means to be loaded by immersion and the retaining member to keep the hair strands on the applicator means while the device is in use. Another attempt is shown in US2003/0024544 wherein a device is disclosed provided with a cavity for the hair product and a retention member which is elastically deformable. The retention member may comprise porous or fibrous material and the cavity is provided with at least one notch to keep the hair strands in position during the application of the hair treatment composition. However the use of such members has a number of drawbacks, in particular the deposition of the composition is not uniform across all the hair strands and or may excessively coat the hair or not coat some hair strands at all. Moreover, the composition may also be displaced from the applicator causing mess.

It is generally recognized that the self-application of a composition to achieve hair strand effects are difficult per se, in particular those for highlighting and dyeing. To achieve the expected end results, an applicator capable of facilitating the self-application of a hair treatment composition needs to be conceived to address several technical challenges but, in particular, the applicator should evenly apply the composition to independent bundles of hair strands. Evenness is very important when the composition is a highlighting or dyeing composition. The permanent effect provided by these compositions is not immediately visible after the application and if the result is not appealing, it is not easily reversed. An applicator should hence ensure homogeneous coating along the length and width of the bundle of hair strands and likewise on the front and rear surfaces.

In addition, such applicators should apply an amount of hair treatment composition, which is sufficient to coat all of the hair strands and thereby provide a hair strand effect without transferring to neighbouring strands or the scalp and skin. Furthermore, the applicator should not apply but then subsequently scrape off the hair treatment composition while the user moves the applicator along the bundle of hair strands. The application with such an applicator should also occur in a tidy and clean fashion without the hair treatment composition leaking out of the hair treatment applicator. The applicator should also allow the movement of hair through the applicator without hindering its path resulting in snaring, entanglement and potentially discomfort to the user.

Finally, such an applicator for hair treatment compositions should be easy to use; it should be cheap and easy to manufacture and it should not require any special experience and training in matters such as how much and where to load the hair treatment composition. Ideally, the consumer should be able to load and use the applicator by simply following a few instructions provided by the manufacturer.

It has now been found that an applicator, as defined herein after can significantly improve the application of a hair treatment composition to provide hair strand effects.

SUMMARY OF THE INVENTION

According to the invention an applicator (1) for applying a hair treatment composition to the hair, wherein said applicator (1) comprises a plate (10) and a well (20), wherein said plate (10) and well (20) are movably joined by a connection (30) so that the applicator (1) may alternate between a closed and an open state, and wherein said plate (10) has an external surface (102) and an internal surface (101), and said internal surface (101) comprises a first fin, (70) which projects from said internal surface (101), and a second fin (71) which projects from said internal surface (101), wherein said first and second fins (70, 71) each independently has a free distal edge (80, 81), wherein said free distal edge (80) of said first fin (70) points towards said free distal edge (81) of said second fin (71); and wherein said well (20) comprises a base (201), a wall (202) emerging from said base (201) and a rim (222) and wherein said applicator (1) further comprises a fluid metering means, wherein said fluid metering means comprises a lower metering means (50) positioned on the internal surface of said wall (202) adjacent said rim (222) and which extends from the internal surface of said wall (202) towards the centre of said well (20), wherein when said applicator (1) is in said closed state, said lower metering means (50) and said first fin (70) are substantially juxtaposed to provide said fluid metering means.

Furthermore, the present invention relates to a method of applying a hair treatment composition to the hair with an applicator according to the present invention, whereby a hair treatment is applied to said applicator in an open state, selecting a bundle of hair and placing the hair strands in said applicator. The applicator is brought into a closed position and then swiped along the length of the hair strand.

The present invention also relates to a kit of parts comprising an applicator according to the present invention and one or more individually packaged hair treatment compositions and instructions for use thereof.

DETAILED DESCRIPTION OF THE INVENTION

For the purpose of this invention, the term hair refers to both living hair i.e. on a living body and to non-living hair i.e. in a wig, hairpiece or other aggregation of non-living keratinous fibre. Mammalian, preferably human hair is intended.

For the purpose of this invention, the term "laid upon" is generally used to indicate the location of the feature to which it refers and not the act of locating it.

The present invention is characterized by the synergistic relationship that the features as described herein have when combined together in the specific relationship selected within the present invention to solve the above technical problem.

Figure 1:
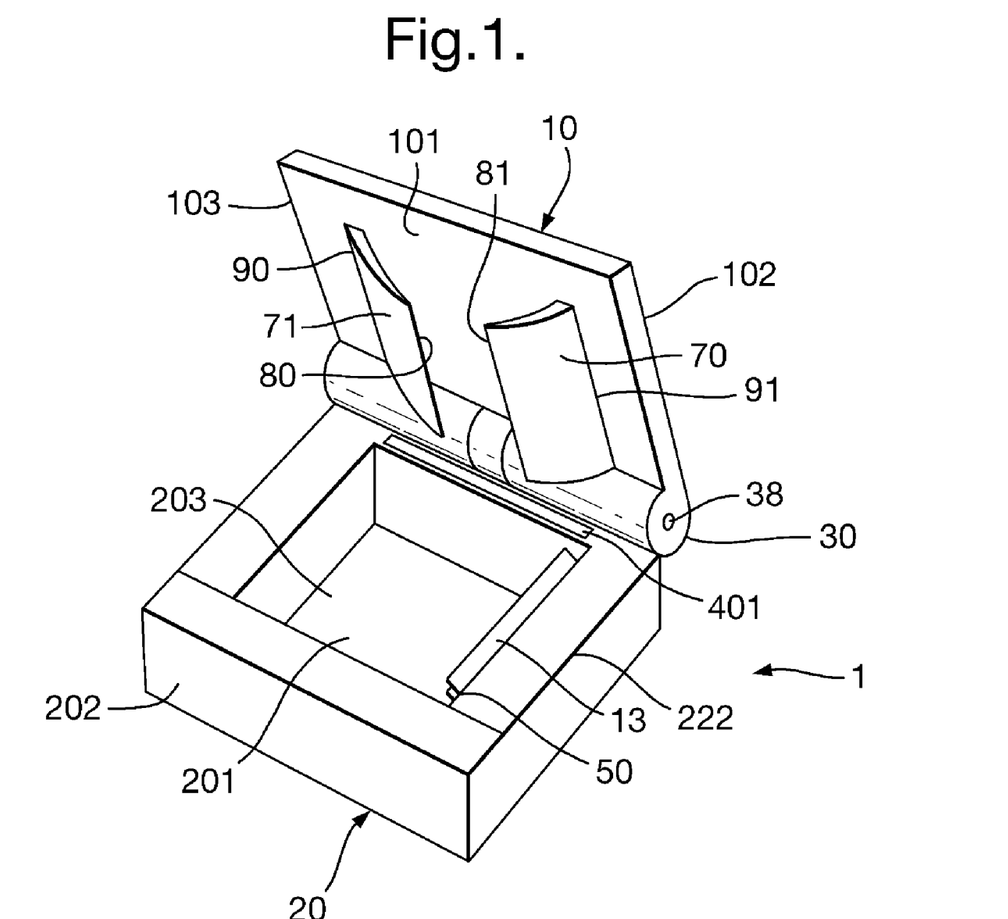
FIG. 1 is a perspective view of an embodiment of said applicator (1) according to the invention. Said applicator comprises a plate (10), a well (20) and a connection (30). The well comprises a base (201) and a wall (202) emerging from said base (201) and a rim (222). In this embodiment, a lower metering means (50), is positioned upon the internal surface of said wall (202) of said well (20) adjacent said rim (222) and extends towards the centre of the well (20). A first and a second fin (70, 71) project from said internal surface (101) of said plate (10). The applicator (1) is shown herein in an open state, whereby said internal surface (101) of said plate (10) is in a distant relationship to said opening (203) of said well (20). On the base (201) of said well (20) adjacent to said wall (202) at the side of the connection (30) said applicator (1) comprises a sealing means (401).

To achieve the technical effect described herein, the applicator (1) for applying a hair treatment composition to the hair according to the present invention comprises a plate (10) and a well (20) as shown in FIG. 1. A connection (30) movably joins said plate (10) to said well (20). Said plate (10) comprises a perimeter (103) and an internal (101) and an external surface (102). Said well (20) is formed by a base (201) and a wall (202), said wall (202) emerging from said base (201) and extending upwardly. Said wall (202) comprises a rim (222), said wall (202) and said rim (222) define an opening (203) of said well (20) as shown in FIG. 1. Said plate (10) and said well (20) are movably joined by said connection (30), so that said applicator (1) can alternate from an open state to a closed state. In this latter state, said internal surface (101) of said plate (10) is in a juxtaposed relationship to said opening (203) of said well (20).

Said internal surface (101) of said plate (10) further comprises a first fin (70) and a second fin (71) which project from said internal surface (101). The distal edge (80) of said first fin (70) points towards the distal edge (81) of said second fin (71). Said applicator (1) further comprises a fluid metering means which comprises a lower metering means (50). Said lower metering means (50) is positioned on the internal surface of said wall (202) adjacent said rim (222), wherein said lower metering means (50) extends from the internal surface of said wall towards the centre of said well (20). Said lower metering means (50) and said first fin (70) are positioned such that when said applicator (1) is in said closed state, said lower metering means (50) and said first fin (70) are substantially juxtaposed to provide said fluid metering means. Preferably said lower metering means (50) and said second fin (71) are also positioned such that when said applicator (1) is in said closed state, said lower metering means (50) and said second fin (71) are substantially juxtaposed to provide said fluid metering means.

The combination of said first and second fins (70, 71) and fluid metering means comprising a lower metering means (50) as described below, enable said applicator (1) to perform an application of a hair treatment composition to a hair strand, not only in a clean and non-messy fashion, but also evenly to provide an effective hair strand effect.

1. Applicator

The applicator (1) according to the present invention comprises a plate (10) movably joined to a well (20). Said plate (10) and said well (20) of said applicator (1) according to the invention are of ergonomic size and can thus fit easily on either hand. Said internal surface (101) preferably has a surface area of from about 2 cm$^2$ to about 150 cm$^2$, preferably from about 2 cm$^2$ to about 70 cm$^2$, more preferably from about 3 cm$^2$ to about 50 cm$^2$ and even more preferably from about 4 cm$^2$ to about 30 cm$^2$. The shape of said plate (10) may vary. Rectangular, square, circular, elliptical, oblong shape or combination thereof may be useful as they are easy to manufacture but other shapes, particularly those that are easily recognized by the consumers may also be used.

Said plate (10) of said applicator (1) comprises an axis Y. Axis Y extends straight from the centre of said plate (10) and transversally crosses said connection (30), preferably substantially perpendicular to said connection (30).

Said plate (10) comprises a perimeter (103), an internal surface (101) and an external surface (102). Said well (20) comprises a base (201), a wall (202) and said wall (202) comprises a rim (222). Said rim (222) defines an opening (203) and an internal volume of said well (20). Said internal volume is preferably for containing a hair treatment composition. Said wall (202) comprises an internal and an external surface.

Preferably, said perimeter (103) of said plate (10) and said rim (222) of said wall (202) of said well (20) may be curvilinear or sharp. Said perimeter (103) of said plate (10) and said rim (222) of said wall (202) of said well (20) have each independently a length. Preferably, said perimeter (103) and said rim (222), have substantially identical lengths. Said rim (222) also comprises a width. Preferably, said width of said rim (222) is from about 1 mm to about 20 mm, more preferably from about 2 mm to about 15 mm, even more preferably from about 3 mm to about 8 mm.

Figure 2:
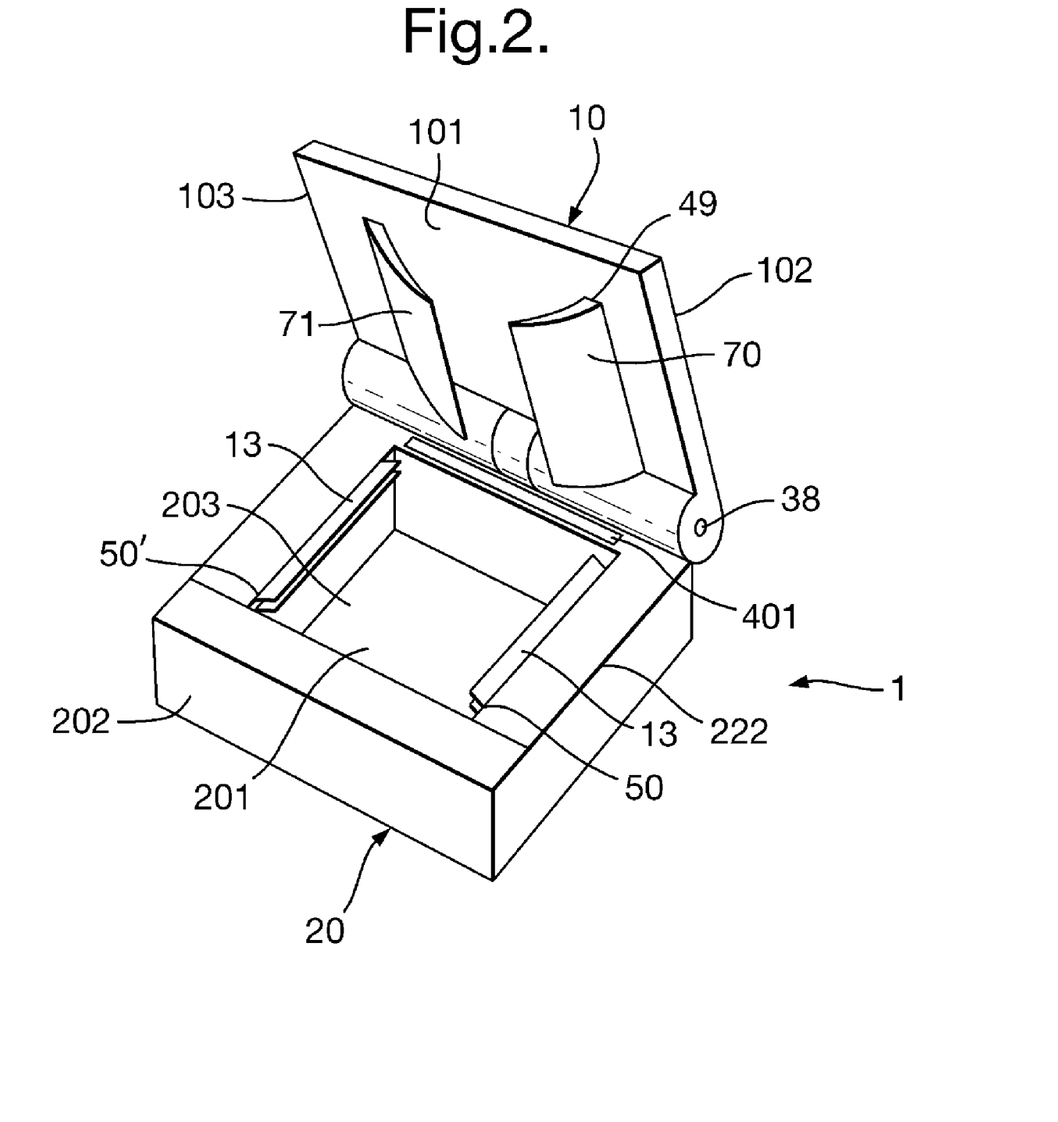
FIG. 2 is a perspective view of an embodiment of said applicator (1) according to the invention. Said plate (10) is movably joined to said well (20) by a connection (30). A first and a second fin (70, 71) project from said internal surface (101) of said plate (10). A lower metering means (50) is positioned upon the internal surface of said wall (202) adjacent said rim (222) in two portions (50, 50'), adjacent the ends of said connection (30).

Said internal surface (101) of said plate (10) may be substantially flat as shown in FIGS. 1 and 2 or may be concave, convex or have a waved pattern. Said external surface (102), said wall (202) and said bottom (201) may also be substantially flat, concave, convex or waved. Preferably, said base (201) of said well (20) is substantially flat.

Said plate (10) and said well (20) may be manufactured from any known material or combination of materials capable of supporting a hair treatment composition. Suitable materials are polymer resins such as a polyolefins e.g. polypropylene, polyethylene or polyethylene terephthalate. Other materials which could be used include polyvinylchloride, polyamide, acetyl, acrylonitrile butadiene styrene, acrylic, acrylonitrile styrene acrylate, ethylene vinyl alcohol, polycarbonate, polystyrene, silicone or thermo plastic elastomer, thermo plastic vulcanate or copolymers where appropriate; flexible pliable substrates such as paper boards, metal based substrates and aluminium foils, filmic substrates or multiple laminations or combinations of multiple layers of said materials.

The method of manufacture of said plate (10) and said well (20) may include, but is not limited to, injection moulding, co-injection moulding, over moulding, in-mold assembly, compression moulding, blow moulding, thermo or vacuum forming of a blister type shell and lamination onto a carrier plastic or board material in the horizontal or vertical plane.

A connection (30) movably joins said plate (10) and said well (20) such that it is possible for said applicator (1) to alternate from an open state to a closed state. When said device (10) is in a closed state, said lower metering means (50), is in a substantially juxtaposed relationship to said first fin (70).

Said plate (10) and said well (20) are connected via any suitable means that fulfils the above described requirements for a connection (30), including the user's hand, for example through the thumb and index finger. In one embodiment, said plate (10) and said well (20) are mounted at the ends of the arms of a tweezers-like or tong-like connection (30). In another embodiment said plate (10) and said well (20) are connected via one or more hinges, preferably one hinge. Preferably, said connection (30) is contiguous and located adjacent to said perimeter (103) of said plate (10) and to said rim (222) of said well (20).

A connection (30) is necessary to improve the user's perception of control over the applicator (1) and to allow the user to guide the applicator (1), with the use of either hand, precisely and easily to each bundle of hair strands.

2. Fins

The applicator (1) according to the invention comprises a first fin (70) and a second fin (71), which independently project from said internal surface (101), preferably from said substantially flat internal surface (101) of said plate (10). The distal edge (80) of said first fin (70) points towards the distal edge (81) of said second fin (71). The term "fin" within the scope of the present invention defines a strip or sheet of material, preferably of substantially constant thickness as described below. The form of said first (70) and second (71) fin may vary; preferably said first (70) and second (71) fin have the form of a parallelepiped wherein two of the six faces extend for an area which is at least two times greater, more preferably five times greater, than the area of any of the other four faces. Those two faces have preferably a substantially flat surface. The shape of said first (70) and second (71) fin may vary. Rectangular, square, circular, elliptical, oblong or combination thereof may be useful. A rectangular shape as shown in FIGS. 1 and 2 is preferred.

As shown in FIG. 1, a first fin (70) projects from said internal surface (101), preferably substantially flat internal surface of said plate (10) and extends for an average first length (L1) of from about 1 mm to about 50 mm, preferably from about 2 mm to about 25 mm, more preferably from about 3 mm to about 15 mm. A second fin (71) projects from said internal surface, preferably said substantially flat internal surface (101) of said plate (10) independently from said first fin (70) as shown in FIG. 2, and extends independently from said first fin (70) for an average second length (L2) of from about 1 mm to about 50 mm, preferably from about 2 mm to about 25 mm, more preferably from about 3 mm to about 15 mm.

Preferably said first (70) fin and said second (71) fins project independently from said internal surface (101) of said plate (10) and extend with substantially identical average first and second lengths (L1; L2). Each of said first (70) and second (71) fin has a distal edge and a proximal edge. Said proximal edge are those attached to said internal surface (101) of said plate (10) as shown in FIG. 2. The distal edge (80) of said first fin (70) points towards the distal edge (81) of said second fin (71). Said proximal edges are each independently delimited by an average width (W1) for said first fin (70) and an average width (W2) for second fin (71) and each independently by average thickness (T1) for said first fin (70) and an average thickness (T2) for said second fin (71). Said average width (W1) and (W2) are preferably of from about 20 cm to about 0.5 cm, more preferably from about 15 cm to about 1.0 cm and even more preferably from about 10 cm to about 1.5 cm. Said average thicknesses (T1) and (T2) are preferably from about 5 mm to about 0.1 mm, more preferably from about 4 mm to about 0.5 mm, even more preferably from about 3 mm to about 0.5 mm. Preferably, said distal edges have also substantially identical average widths (W1) and (W2) and substantially identical average thicknesses (T1) and (T2) as those proximal edges. Said first and second fins (70; 71) may have protrusions or may be embossed, especially to provide visual or tactile decoration.

Preferably said first (70) and second fins (71) are substantially identical and project in a way that said proximal edges (90; 91) are substantially parallel to said axis Y and said distal edges (80; 81) verge one toward the other as shown in FIG. 2. Preferably said proximal edge (90) of said first fin (71), more preferably said proximal edge (90) of said first fin (71) and said proximal edge (91) of said second fin (71) project from said internal surface (101) substantially parallel to said axis Y of said plate (10) as shown in FIG. 2.

Said first and second fins (70, 71) may be provided in a variety of materials as previously described herein to manufacture the plate (10) or well (20) and be manufactured independently of said applicator (1). Preferably said fins are fluid impervious. In certain embodiments, both the said first (70) and second (71) fins and said plate (10) may be manufactured within the same injection or co-injection mould for example from a thermo plastic elastomer.

3. Fluid Metering Means

The applicator (1) according to the present invention is characterized by a fluid metering means comprising a lower metering means (50), preferably selected from at least one resilient convex shaped member or at least one resilient parallelepiped shaped member. Preferably said lower metering means is liquid impervious. Said lower metering means (50) is positioned on the internal surface of said wall (202) of said well (20) adjacent said rim (222) of said well (20), wherein said lower metering means extends from the internal surface of said wall (202) towards the centre of said wall (202). When said applicator (1) is in said closed state, said lower metering means (50) and said first fin (70) are substantially juxtaposed to provide said fluid metering means. Preferably said fins (70, 71) do not touch said base (201) of said well (20) when the applicator (1) is in a closed state. The term resilient as used herein refers to the ability of the fluid metering means to be deformed upon the application of pressure and return to its relaxed position upon release of the pressure.

Without wishing to be bound by theory, it is believed that by having said fluid metering means comprising a lower metering means (50) positioned upon the internal wall (202) of said well adjacent said rim (222) and extending towards the centre of said well, and a first fin and a second fin (71) projecting from said internal surface (101) whereby said lower metering means (50) and said first fin (70) are substantially juxtaposed when said applicator (1) is in a closed state; allows said applicator (1) not only to apply the hair treatment composition, but to evenly apply the composition along the entire hair strand.

Evenness is important in the application of a hair treatment composition, especially when said hair treatment composition is a highlighting composition or a dyeing composition. The permanent effect provided by those compositions is not immediately visible after the application and if the result is not appealing, it is not easily reversed. An applicator should hence ensure homogeneous application along the length, from root to tip, of said bundle of hair strands and likewise also on the front and rear surfaces and across the width of the bundle of hair strands. Therefore, it is not only the amount of hair treatment composition which is applied that is important but also the way it is applied. The applicator (1) according to the invention is not only designed to facilitate the application of a hair treatment composition to a hair strand, preferably to a bundle of hair strands, said applicator (1) also avoids that said hair treatment composition is neither applied in excessive amount nor removed from said hair strand while the applicator (1) is used, so as to obtain a very homogeneous and reproducible application, without the hair movement being impaired by tangling or snagging during use. In particular, the provision of the resilient lower metering means ensures that no pressure points are generated during use that consequently scrapes the composition off the hair. The resilience also ensures that in the absence of hair, in a closed position, the applicator forms a seal at the rim to prevent any composition leaking out, whilst in the presence of hair, it can deform and enable the hair and a controlled amount of composition to pass through.

The lower metering means (50) comprises at least one, preferably at least two resilient convex shaped member or at least one, preferably at least 2, more preferably at least 5 resilient parallelepiped shaped member. A preferred parallelepiped shaped member is a strip (13). The term strip (13) within the scope of the present invention defines a strip (13) or sheet of material, preferably of substantially constant thickness as described below. The form of each of said strip (13) may vary; but preferably each strip (13) has the form of a parallelepiped, wherein two of the six faces extend for an area which is at least twice the area of the other four faces. These two faces have preferably a substantially flat surface. The shape of each of said strips (13) may vary. Rectangular, square, circular, elliptical, oblong or combination thereof may be useful. A rectangular shape as shown in FIG. 2 is preferred.

The strip (13) of said lower metering means (50) is positioned upon said internal surface of said wall (202) adjacent said rim (222) in a continuous or in a discontinuous manner, preferably a continuous manner. By discontinuous is meant that each of said strip (13) may form loci or islets or may be interrupted. In one embodiment, said lower metering means (50) is positioned adjacent the entire rim (222) of said wall (202). In another embodiment, said lower metering means (50) is laid upon only a section or a plurality of sections of the internal surface of said wall (202), for example only a portion of said length of said internal surface of said wall (202) may comprise said lower metering means (50) as shown in FIGS. 1 and 2. Preferably said lower metering means (50) is positioned adjacent to said connection (30), more preferably said lower metering means (50) is positioned adjacent the two ends of said connection (30). Preferably said lower metering means (50) is positioned substantially parallel to said rim (222).

In each embodiment, the lower metering means (50) and the first fin (70) are positioned such that when said applicator is in a closed state said lower metering means (50) and said first fin (70) are substantially juxtaposed. In a particularly preferred embodiment, said lower metering means (50) comprise two portions (50; 50'), said portions (50; 50') are preferably located adjacent the two ends of said connection (30).

In a preferred embodiment, the lower metering means (50) comprises at least one strip (13), preferably from 2 to 20 strips (13), preferably from 4 to 14, more preferably from 6 to 12 strips (13).

In a preferred embodiment said lower metering means (50) comprises two sets of strip (13), wherein each of said sets comprises at least two of said strip (13), preferably 5 strips (13). The strip (13) of said lower metering means (50) are preferably orientated substantially parallel to one another, and more preferably each set of strips (13) comprises strip (13) which are substantially parallel to one another and preferably equidistant from each adjacent strip (13).

Each of said strip (13) of said lower metering means (50) may independently have a length of from about 3 mm to about 40 cm, preferably from about 5 mm to about 10 cm, more preferably from about 8 mm to about 5 cm. Said strip (13) of said lower metering means (50) may independently have a constant or variable width along said lengths. Said strip (13) of said lower (50) metering means may independently have a maximum width of from about 0.1 mm to about 2 mm, preferably from about 0.1 mm to about 1.0 mm, more preferably from about 0.1 mm to about 0.5 mm, a maximum height of from 0.1 mm to 5.0 mm, preferably 0.2 mm to 3.0 mm, more preferably from 0.3 mm to 2 mm. In a preferred embodiment said strips (13) have substantially identical and constant widths and lengths and preferably substantially identical heights.

In an alternate embodiment of the present invention said lower metering means (50), comprises at least two strips (13) wherein each of said strips (13) are not of identical heights. Embodiments include configurations wherein there is a central strip (13) having a maximum height or a minimum height and configurations wherein the height gradually increases to a maximum, which may extend outward or inward of the internal surface of said wall (202) of said applicator (1) and also wherein the strips (13) are positioned on a raised bed which is either substantially horizontal or at a raised angle which may extend outward or inward of the internal surface of said wall (202) of said applicator (1).

According to an alternative embodiment of the present invention, the lower (50) metering means comprises at least one, preferably at least two resilient convex shaped members. Each of said members independently comprise an inner and an outer surface, wherein said outer surface of said lower fluid metering means (50) independently has a convex shape and wherein when said applicator (1) is in said closed state, said lower metering means (50) and said first fin (70) are substantially juxtaposed to provide said fluid metering means. As used herein the term outer surface of the lower metering means (50) refers to surface of the lower metering means which is not in direct contact with the internal surface of said wall (202) and the inner surface refers to the surface in contact with the internal surface of said wall (202).

Said convex shaped member may be positioned on said internal surface of said wall (202) in a continuous or in a discontinuous manner, preferably a continuous manner. By discontinuous is meant that said member may form loci or islets or may be interrupted. In one embodiment, said convex shaped member is laid upon the entire length of the wall adjacent said rim (222), preferably substantially parallel to said rim (222). In another embodiment, said convex member is laid upon only a section or a plurality of sections of the length of said internal surface of said wall (202) adjacent said rim (222). In one embodiment, the convex member may extend along substantially the entire perimeter length of said internal surface of said wall (202) or in another embodiment only a section or a plurality of sections of the perimeter length will comprise said convex shaped member.

Preferably said convex shaped member is positioned adjacent to said connection (30). In each embodiment, however, the convex shaped member is positioned such that when said applicator is in a closed state said convex shaped member and said first fin (70) are substantially juxtaposed. In a particularly preferred embodiment, said lower metering means (50) comprises two portions (50; 50'). Preferably, each of said lower metering means (50) has a substantially semi-elliptical outer surface and more preferably each of said outer surfaces has a semi elliptical cross section across its entire length, which is preferably uniform across the entire length. In the preferred embodiment, said convex shaped member independently have a tubular shape or partially tubular shape and are preferably partially or entirely hollow.

The lower (50) metering means is preferably independently selected from a polymer resin such as a polyolefin e.g. polypropylene, polyethylene or polyethylene terephthalate, polyvinylchloride, ethylene vinyl acetate, polyurethane, polytetrafluoroethylene, polystyrene, natural rubber, latex, nylon, nitrile, silicone; thermo plastic elastomer (TPE) or copolymers where appropriate or thermoplastic elastomers may also be used or a flexible pliable substrate such metal based substrates and aluminium foil, or multiple laminations or combinations of multiple layers of said materials. Preferably, said lower metering means (50) are made from a thermoplastic elastomer. The lower metering means of the present invention may also include composite materials having one or more plies of the same or different materials superimposed physically, joined together continuously (laminated), in a discontinuous pattern, or by bonding the external edges at discrete loci.

Said lower metering means (50) may be attached by any suitable method to said internal surface of said wall (202), providing that said method does not destroy or alter the performance of said metering means (50). Said members for example said strips (13) may or may not be attached to an adjacent member for example a strip (13) or to the member or strip (13) on a set of members or strips (13).

4. Additional Features

The applicator (1) may further comprise one or more sealing means, preferably one sealing means (401) is present within the hair treatment applicator (1). Said sealing means (401) may be located on the bottom (201) of said well (20) adjacent to said wall (202) at the side of the connection (30) or on said internal surface (101) adjacent to said connection (30). Preferably said sealing means (401) is adjacent said connection (30).

The sealing means (401) is provided to avoid displacement of hair treatment composition towards the connection (30) and hair from being trapped within said connection (30) when said internal surface (101) of said plate (10) is brought into a juxtaposed relationship to said opening (203) of said well (20). Useful materials to manufacture a sealing means (401) include those described herein for said first fin (71) and foams.

One or more stop mechanisms may be incorporated onto said applicator (1). The stop mechanism collaborates with said connection (30) to ensure that when said internal surface (101) of said plate (10) is brought into a juxtaposed relationship to said opening (203) of said well (20), the average distance between said perimeter (103) and said rim (222) is controlled. In one embodiment, two stop mechanisms are comprised on said rim (222) of said wall (201) of said well (20), preferably said two stop mechanisms are two substantially identical hemispheres. Useful materials to manufacture a stop mechanism are previously described herein to manufacture the plate (10) or well (20) described herein.

The applicator (1) disclosed herein may further comprise gripping areas on the external surfaces (102) of said plate (10) and/or on said bottom (201) of said well (20). Said gripping areas are designed to provide grip. Gripping means may be provided as fastening means to accommodate the user's fingers.

Fingers may be used to select the hair strands on which the hair treatment composition should be applied. The applicator (1) of the present invention may however be further provided with hair strand selection means. Examples of hair strand selection means are, but not limited to, spikes, hooks, crochets, clips or beads. The hair strand selection means may be incorporated onto said plate (10) and/or said well (20). Said means may also be attached through a snap mechanism to said plate (10) and/or said well (20) such that the hair strand selection means may swing from a position proximal to said plate (10) and/or said well (20) to a far one, such as happens with the blades of a penknife. The hair strand selection means may also be separately provided to the applicator (1) of the present invention as a component of a kit as described herein below.

5. Method of Use

The present invention also relates to a method to apply a hair treatment composition with said applicator (1) according to the invention to a hair strand, preferably a bundle of hair strands, wherein said applicator (1) comprises said hair treatment composition and whereby said hair strand is contacted with said applicator (1). Said applicator (1) may be preloaded with one or more hair treatment compositions, but preferably one or more hair treatment compositions are loaded into said applicator (1) before the contact of said hair strand, preferably said bundle of hair strands, with said applicator (1).

The hair treatment compositions may be a single hair treatment composition or may be formed by a first hair treatment composition which requires mixing with a second hair treatment composition before application to the hair. Preferably, said first and second hair treatment compositions are mixed to form a third hair treatment composition. Said third hair treatment composition is loaded in said hair treatment applicator (1) before contacting the hair strand, preferably a bundle of hair strands, with said hair treatment applicator (1).

Once the hair treatment applicator (1) is loaded with one or more hair treatment compositions, the user holds through the external surfaces (102) of said plate (10) and bottom (201) of said well (20) of said applicator (1) in one hand, preferably between the thumb and the index finger. Once the user has selected the hair strands to be treated, said hair strand, preferably said bundle of hair strands, is located between said plate (10) and said containment portion (20) while the applicator (1) is in an open state. Subsequently said internal surface (101) of said plate (10) is brought into a juxtaposed relationship to said opening (203) of said well (20). Said applicator (1) is swiped along the length of said hair strand, preferably on said bundle of hair strands, and one or more hair treatment compositions are applied. More preferably, said hair treatment applicator (1) is located at the root-line of said hair strand, preferably at the root-line of said bundle of hair strands. The hair treatment composition may also be applied only to limited areas of the hair, i.e. the user can coat only the root-line with the hair treatment composition. The swiping may be repeated more than once, preferably twice.

Finally, the application of the hair treatment composition may occur on wet or dry hair and optionally, a rinsing or a shampooing step can be included between application of the first and second compositions to the hair.

6. Hair Treatment Compositions, Use Thereof and Kit

The present invention further comprises a kit. Said kit comprises an applicator (1) according to the invention and one or more individually packaged hair treatment compositions. Preferably, these compositions are selected from the group consisting of styling compositions, dyeing compositions, highlighting compositions or combination thereof. Each of these hair treatment compositions or combinations thereof may be used to provide a hair strand effect with said applicator (1) described above. More preferably, said one or more hair treatment composition is a highlighting composition.

Examples of hair treatment compositions which can be used with the hair treatment applicator (1) according to the invention are indicated below in table 1 The hair treatment compositions may comprise components known, conventionally used, or otherwise effective for use in hair treatment compositions particularly oxidative bleaching and dye compositions which include but are not limited to: developer dye compounds; coupler dye compounds; direct dyes; oxidizing agents; reducing agents; thickeners; chelants; pH modifiers and buffering agents; alkalising agents, carbonate ion sources and radical scavenger systems; glycine; amodimethicone, ethylenediamine disuccinic acid; anionic, cationic, non-ionic, amphoteric or zwitterionic surfactants, or mixtures thereof; anionic, cationic, non-ionic, amphoteric or zwitterionic polymers, hydrophobically modified polymers or mixtures thereof; fragrances; dispersing agents; solvents, peroxide stabilizing agents; chelants, humectants, proteins and derivatives thereof, plant materials (e.g. aloe, chamomile and henna extracts); silicones (volatile or non-volatile, modified or non-modified), film-forming agents, cellulose polymers and their derivatives, ceramides, preserving agents, gel networks, colour indicators and opacifiers. Some adjuvants which are suitable are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions) are useful in identifying specific adjuvants to achieve a particular purpose or multipurpose. A representative but not exhaustive list of polymers and thickening agents can be found in "The Encyclopaedia of Polymers and Thickeners for Cosmetics" compiled and edited by Robert Y. Lochhead, PhD and William R. Fron, Department of Polymer Science, University of Southern Mississippi.

The present invention further comprises a kit. Said kit comprises an applicator (1) as described above and one or more individually packaged hair treatment compositions. More than one applicator (1) may be comprised in said kit.

In one embodiment of the present invention, said one or more individually packaged hair treatment compositions comprise a first individually packaged hair treatment composition and a second individually packaged hair treatment composition. When mixed said first and second individually packaged hair treatment compositions form a third hair treatment composition. Examples of such compositions include so called semi-permanent and permanent colorants which typically contain oxidative dyes and an oxidant, and highlighting compositions containing an oxidant and an alkalising agent, optionally with a persulfate salt. Preferably, said first individually packaged composition comprises an oxidizing agent and said second individually packaged composition comprises an alkalizing agent. Preferably, said oxidizing agent is hydrogen peroxide. More preferably, at least one of said first and/or second individually packaged hair treatment composition comprises a persulfate salt.

In one embodiment of the kit according to the present invention said first individually packaged hair treatment composition comprises from 3% to 12% of hydrogen peroxide by weight of said first individually packaged hair treatment composition and said second individually packaged hair treatment composition is in the form of a powder or paste activator and said second individually packaged hair treatment composition comprises from 10% to 60% of persulfate salt selected from sodium persulfate, potassium persulfate, ammonium persulfate or mixtures thereof, by weight of said second individually packaged hair treatment composition. Said kit optionally comprises a third individually packaged hair treatment composition comprising from 3% to 25% of an alkalizing agent in an aqueous vehicle, by weight of said third individually packaged hair treatment composition.

In another embodiment of the present invention said first individually packaged hair treatment composition comprises from 1.5% to 12% of hydrogen peroxide by weight of said first individually packaged hair treatment composition and said second individually packaged hair treatment composition comprises from 0.01% to 6% of a dye selected from direct dyes, oxidative dye precursors, oxidative dye couplers or mixtures thereof, by weight of said second individually packaged hair treatment composition.

Additional individually packaged hair treatment compositions may be present in the kit and may comprise shampoos, conditioner or styling products.

The applicator embodiments described hereinabove when utilised with each of the compositions described herein below, provide a simple and easy application resulting in an even application of the composition on the hair, whilst not causing any consumer discomfort or snagging.

A hair bleaching composition was prepared by mixing about 45 g of any of the formulations of Phase 1 (1.1, 2.1, 3.1, 4.1, table 1), which were in a liquid form with about 15 g of any of the formulations of Phase 2 (1.2, 2.2, 3.2, 4.2, in table 1), which were in a powder form. Mixing was achieved as follows: the powder formulation of Phase 2 was placed into a mixing tray and the liquid formulation of Phase 1 was poured on top of the powder. The two formulations were then mixed together using a spatula to form a bleaching composition. Mixing was completed when the bleaching composition looked visually homogeneous.

TABLE 1

Formulations of Phase 1 and 2 which can be mixed to form a highlighting composition.

| Phase 1 | 1.1 | 2.1 | 3.1 | 4.1 |
|---|---|---|---|---|
| De-ionized Water | q.s. to 100% | q.s. to 100% | q.s. to 100% | q.s. to 100% |
| Hydrogen Peroxide (35% Active) | 17.2 | 17.2 | 17.2 | 17.2 |
| Disodium EDTA | 0.04 | 0.04 | 0.04 | 0.04 |
| Sodium Hydroxide (50% aq. Solution) | q.s. to pH 3.5 | q.s. to pH 3.5 | q.s. to pH 3.5 | q.s. to pH 3.5 |
| Stearyl Alcohol [1] | 2 | 1 | 2 | 2 |
| Cetyl Alcohol [2] | 3 | 1.5 | 3 | 3 |
| Ceteareth 25 [3] | 1.5 | 0.75 | 1.5 | 1.5 |
| Aculyn ™ 33 [4] | | 2.4 | | |
| Salcare ™ SC 90 [5] | | | 1 | |
| Phase 2 | 1.2 | 2.2 | 3.2 | 4.2 |
| Ammonium Persulfate | 28.6 | 28.6 | 28.6 | 28.6 |
| Potassium Persulfate | 50 | 50 | 50 | 47 |
| Sodium Persulfate | 7.14 | 7.14 | 7.14 | 7.14 |
| Sodium Metasilicate | 14.26 | 14.26 | 14.26 | 14.26 |
| Carbopol ™ Ultrez 10 [6] | | | | 3 |

All ingredients are in percentage by weight of the formulation phase.
[1] Stearyl Alcohol Crodacol S-95, Croda, Inc.
[2] Cetyl Alcohol, Crodacol C-70, Croda, Inc.
[3] Cetearth 25, Cremophor A 25, BASF Corporation
[4] Aculyn ™ 33, Rohm and Hass Company Inc.
[5] Salcare ™ SC 90 Ciba Specialty Chemicals Corporation
[6] Carbopol ™ Ultrez 10

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An applicator (1) for applying a hair treatment composition to the hair, wherein said applicator (1) comprises a plate (10) and a well (20), wherein said plate (10) and well (20) are movably joined by a connection (30) so that the applicator (1) may alternate between a closed and an open state, and wherein said plate (10) has an external surface (102) and an internal surface (101), and said internal surface (101) comprises a first fin (70) which projects from said internal surface (101) and a second fin (71) which projects from said internal surface (101), wherein said first fin (70) and second fin (71) each independently comprise a free distal edge (80, 81), wherein said free distal edge of said first fin (70) points towards said free distal edge (81) of said second fin (71),
and wherein said well (20) comprises a base (201), a wall (202) emerging from said base (201) and a rim (222)
and wherein said applicator (1) further comprises a fluid metering means, wherein said fluid metering means comprises a lower metering means (50) positioned on the internal surface of said wall (202) adjacent said rim (222) and which extends from the internal surface of said wall (202) towards the centre of said well (20), wherein when said applicator (1) is in said closed state, said lower metering means (50) and said first fin (70) are substantially juxtaposed to provide said fluid metering means.

2. The applicator (1) according to claim 1, wherein when said applicator is in said closed state, said second fin (71) and said lower metering means (50) are substantially juxtaposed.

3. The applicator (1) according to claim 1, wherein said lower metering means (50) comprises at least one strip (13).

4. The applicator (1) according to claim 1, wherein said lower metering means (50) is selected from polymer resins, thermo plastic elastomers (TPE) or copolymers, closed or open cell foams of polyurethane and or combinations of multiple layers of said materials.

5. The applicator (1) according to claim 3, wherein said lower metering means (50) is continuous.

6. The applicator according to claim 3, wherein each of said strips (13) of said lower metering means (50) are substantially parallel to one another.

7. The applicator according to claim 3, wherein each of said strips (13) of said lower metering means (50) are substantially equidistant from each adjacent strip (13).

8. The applicator according to claim 1, wherein said lower metering means (50) is liquid impervious.

9. The applicator according to claim 3, wherein said lower metering means comprises from 2 to 6 strips.

10. The Applicator according to claim 1, wherein said lower metering means (50) is positioned substantially parallel to said rim (222) of said well (20).

11. A method to apply a hair treatment composition with said applicator (1) according to claim 1, to a hair strand, wherein said method comprises applying a hair treatment composition to said applicator (1) in said open state, selecting a bundle of hair strands, placing said hair strands in said applicator (1) and bringing said applicator (1) into said closed position and then swiping said along the length of said hair strand.

12. A kit-of parts comprising an applicator (1) according to claim 1; and one or more individually packaged hair treatment compositions, and instructions for use thereof.

13. Use of an applicator (1) according to claim 1, with one or more hair treatment compositions or combinations thereof to provide a hair strand effect wherein the applicator (1) is loaded with said one or more hair treatment compositions prior to providing the hair strand effect.

* * * * *